United States Patent
Olson et al.

[11] Patent Number: 6,038,473
[45] Date of Patent: Mar. 14, 2000

[54] DEFIBRILLATOR BATTERY WITH DUAL CELL STACK CONFIGURATION

[75] Inventors: Kenneth F. Olson, Edina; Byron L. Gilman, Minnetonka; Gary B. Stendahl, Crystal, all of Minn.

[73] Assignee: SurVivaLink Corporation, Minneapolis, Minn.

[21] Appl. No.: 09/057,133

[22] Filed: Apr. 8, 1998

Related U.S. Application Data

[60] Provisional application No. 60/044,657, Apr. 8, 1997.

[51] Int. Cl.[7] ............................. A61N 1/39; H02J 15/00
[52] U.S. Cl. ........................... 607/5; 320/150; 320/116
[58] Field of Search ........................... 607/2, 29, 34, 607/36, 5, 1; 320/117, 150, 116

[56] References Cited

U.S. PATENT DOCUMENTS

| | | | |
|---|---|---|---|
| 1,319,164 | 10/1919 | Montelius | 320/117 |
| 3,286,152 | 11/1966 | Noe | 320/117 |
| 3,783,877 | 1/1974 | Bowers | 607/34 |
| 3,865,101 | 2/1975 | Saper et al. | 607/5 |
| 3,871,383 | 3/1975 | Lee | 607/34 |
| 4,323,075 | 4/1982 | Langer | 607/5 |
| 4,424,476 | 1/1984 | Mullersman | 320/150 |
| 5,224,870 | 7/1993 | Weaver et al. | |
| 5,343,137 | 8/1994 | Kitaoka et al. | 320/150 |
| 5,350,317 | 9/1994 | Weaver et al. | |
| 5,407,444 | 4/1995 | Kroll | 607/5 |
| 5,411,538 | 5/1995 | Lin | 607/36 |
| 5,470,343 | 11/1995 | Fincke et al. | |
| 5,483,165 | 1/1996 | Cameron et al. | |
| 5,600,227 | 2/1997 | Smalley | 320/150 |
| 5,741,305 | 4/1998 | Vincent et al. | |
| 5,853,908 | 12/1998 | Okutoh | 320/150 |

FOREIGN PATENT DOCUMENTS

WO 97/42669  11/1997  European Pat. Off. .

*Primary Examiner*—Kennedy J. Schaetzle
*Attorney, Agent, or Firm*—Patterson & Keough, P.A.

[57] ABSTRACT

A defibrillator battery pack comprises a housing having a first set of battery cells having an upper set and a lower set of cells and a second set of battery cells connected in parallel with one of the upper or the lower sets of the first set of battery cells. The first set of battery cells is used for charging a capacitor bank of a defibrillator. The second set of battery cells cannot be used for charging and is only used for developing a nominal 5 volts to drive a microprocessor and other circuitry components of an electrical control system of the defibrillator. This arrangement increases the life of the battery pack in the lower voltage range, which is advantageous for operating the microprocessor. This arrangement also maintains the intelligence of the electrical control system because the battery cells supplying power to the microprocessor will always fail after, and not before, failure of the battery cells supplying power for charging the capacitor bank.

10 Claims, 5 Drawing Sheets

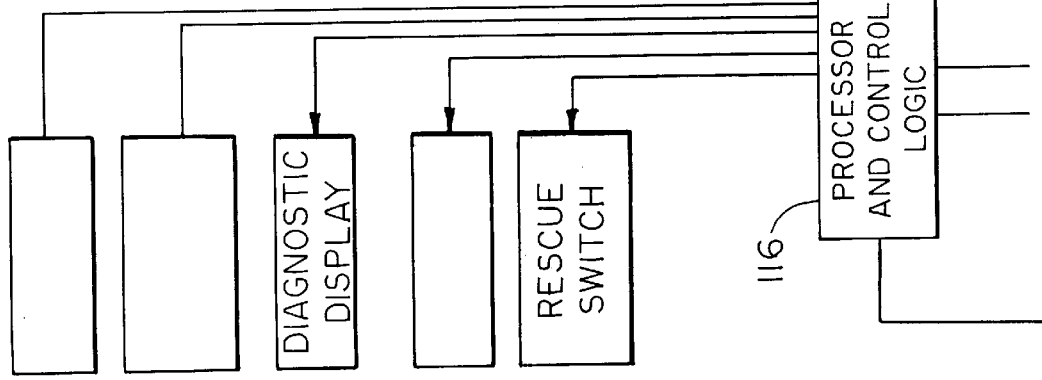

DEFIBRILLATOR BATTERY WITH DUAL CELL STACK CONFIGURATION

RELATED APPLICATION

The present invention is related to U.S. Provisional Patent Application Ser. No. 60/044,657, filed Apr. 8, 1997, the content of which is herein incorporated by reference, and priority to which is claimed according to 35 U.S.C. §119(e).

BACKGROUND OF THE INVENTION

The present invention relates generally to defibrillators. In particular the present invention relates to a dual cell battery stack configuration for use with a defibrillator.

Cardiac arrest, exposure to high voltage power lines and other trauma to the body can result in ventricular fibrillation which is the rapid and uncoordinated contraction of the myocardium. The use of external defibrillators to restore the heart beat to its normal pace through the application of an electrical shock is a well recognized and important tool in resuscitating patients. External defibrillation is used in emergency settings in which the patient is either unconscious or otherwise unable to communicate.

Automated external defibrillators (AED) are used by first responders such as police officers, paramedics and other emergency medical technicians to resuscitate cardiac arrest patients. The AEDs carried by these technicians must be quickly operational after powering up and must not provide false alarms that might delay rescue. In a high stress situation of cardiac arrest, the technician must be able to rely on the operability of the AED. Studies have shown that the chances of successfully resuscitating the patient decreases approximately ten percent per minute following cardiac arrest.

A defibrillation shock electrical pulse selectively applied to a patient is generated within a defibrillator by high voltage generation circuits with energy stored within a capacitor bank of the defibrillator. The capacitor bank forms part of an electrical system along with the battery pack which provides the energy to be stored in the capacitor banks. These shock pulses carry a considerable amount energy of about 200 to 400 joules. This energy, and the generation of the shock pulse, can be dangerous if not handled properly. Accordingly, maintaining control of this potent electrical force under all conditions is imperative.

A microprocessor is typically used to control a defibrillator and its supporting electrical system for charging and generating the shock pulse. Failure of the microprocessor during charging of a capacitor bank or during application of a shock pulse can be detrimental to the patient since the microprocessor would cease control of the charging or application of the shock pulse. The most basic step in maintaining control of the defibrillator with the microprocessor includes maintaining a reliable supply of power to the microprocessor to insure its operation.

Known defibrillator battery packs have a plurality of battery cells connected in series with multiple sets of cells arranged in parallel. For example, as shown in FIG. 1, a prior art battery pack 5 includes two sets of four battery cells with a first set 7 of battery cells (6A–6D) and a second set 8 of battery cells (6A–6D) connected in parallel. Diodes 9 are arranged at the top of each set of cells. These diodes protect the cells from attempts to charge each other.

A microprocessor of the defibrillation device can be powered by a 5 V supply generated with an external regulator connected to the 12 V cell arrangement. Due to inherent inefficiencies, this method wastes energy and can result in a loss of the 5 V supply when the 12 V supply is lost due to battery depletion or other battery failure. When the voltage of the 12 V cell arrangement fluctuates or dips considerably, the 5 V supply drops below a level sufficient to operate the microprocessor. This voltage drop can cause the microprocessor to malfunction and to no longer control operation of the defibrillation device. Significantly, this lack of control includes no longer controlling the capacitor charging operation already in process. With the microprocessor no longer functioning, the capacitor charging operation continues without regulation by the microprocessor resulting in a charged capacitor bank without safe constraint. Accordingly, a nonfunctioning microprocessor due to a failed battery cell can cause a dangerous condition of having a fully charged defibrillator device with no safety controls or result in misapplication of an ongoing defibrillation shock to a patient.

The use of lithium battery cells in defibrillator battery packs carries additional special considerations. For example, when using lithium sulfur dioxide battery cells, it is critical that the cells not be reversed biased. Reverse biasing can occur if the cells are not properly arranged when connected in parallel and if one attempts to recharge the lithium battery cells in the typical battery pack configuration. If the lithium battery cells become reversed biased, overheating will occur in an irreversible battery cell damaging process. Overheating of the cells causes pressure to build up inside the cells until a violent and noxious outgasing occurs. This battery characteristic limits unrestricted transportation of conventional lithium battery cell packs and the manner of their deployment. Accordingly, lithium battery cells for use in a conventional battery pack configuration require special handling.

SUMMARY OF THE INVENTION

A defibrillator battery pack of the present invention comprises a housing having a first set of battery cells having an upper set and a lower set of cells and a second set of battery cells connected in parallel with at least one cell of the first set of battery cells. The first set of battery cells is used for charging a capacitor bank of a defibrillator. The second set of battery cells cannot be used for charging and is only used for developing a nominal 5 volts to drive a microprocessor and other circuitry components of an electrical control system of the defibrillator. This arrangement effectively increases the life or energy capacity of the battery in the lower voltage range necessary for operating the microprocessor and permits the elimination of two battery cells that would otherwise be required in a conventional defibrillator battery pack. Moreover, even when the battery pack does not have enough voltage to adequately charge the capacitor banks of the defibrillator for delivering a shock, the second set of battery cells are available to drive the microprocessor and maintain the intelligence of the electrical control system. In other words, the battery cells supplying power to the microprocessor will always fail after, and not before, a failure of the battery cells supplying power for charging the capacitor bank. This feature insures a safe and graceful shutdown of the microprocessor.

DETAILED DESCRIPTION OF THE DRAWINGS

Figure 2:
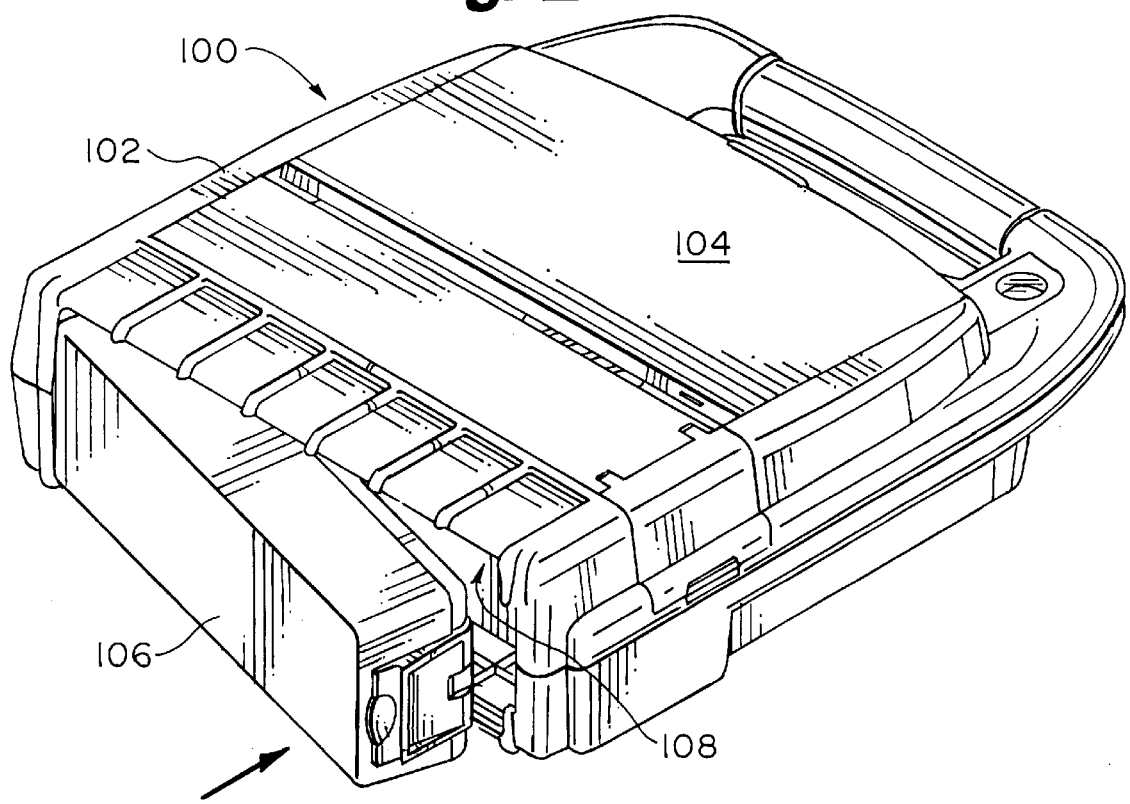
FIG. 2 is a perspective view of an automated external defibrillator incorporating a dual cell defibrillator battery pack of the present invention.

A defibrillator battery of the present invention is preferably adapted for use with an automated external defibrillator (AED). An AED 100 in accordance with the present invention is illustrated generally in FIG. 2. As shown in FIG. 2, defibrillator 100 includes plastic case 102 and a pair of electrodes (not shown) located under openable and closable lid 104 for placement on a patient for delivering a defibrillation shock with AED 100. Defibrillator battery pack 106 of the present invention for powering AED 100 is removably insertable into battery receptacle 108 of AED plastic case 102.

AED 100 is used for emergency treatment of victims of cardiac arrest and is typically used by first responders. AED 100 automatically analyzes a patient's cardiac electrical signal and advises the user to shock a patient upon detection of: (1) ventricular fibrillation; (2) ventricular tachycardia; (3) or other cardiac rhythms with ventricular rates exceeding 180 beats per minute and having amplitudes of at least 0.15 millivolts. When such a condition is detected, AED 100 will build up an electrical charge for delivery to the patient to defibrillate the patient with a defibrillation shock. The operator of AED 100 is guided through the application of a defibrillation shock by voice prompts, an audible charging indicator tone, and an illuminated rescue (shock) initiation button. Olson et al U.S. Pat. No. 5,645,571 discloses the general construction and manner of use of an AED, is hereby incorporated by reference, and is commonly assigned to the assignee of the present application.

Figure 3B:
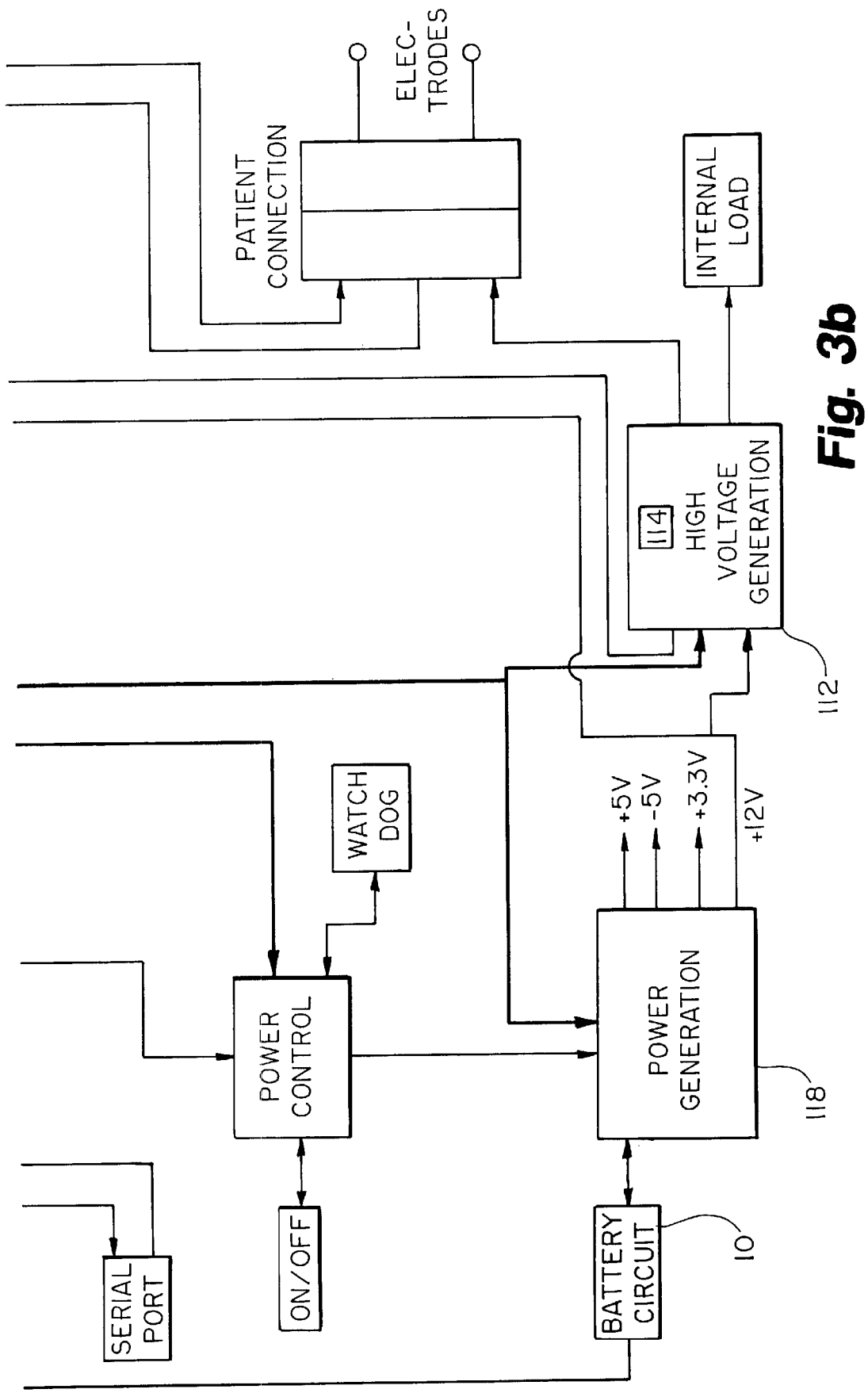
FIG. 3 is a schematic illustration of an electrical system of an automated external defibrillator incorporating a battery circuit of the present invention.

As shown in FIG. 3, AED 100 incorporates electrical system 110 including high voltage generation circuit 112 with capacitor bank 114 for charging and delivering a defibrillation shock pulse to the patient, as is known in the art. Microprocessor 116 of AED electrical system 110 controls capacitor bank 114 of circuit 112 and the accompanying electrical system components shown in FIG. 3. Battery circuit 10 of the present invention is electrically connected to at least microprocessor 116, and power generation circuit 118, which is in turn electrically connected to high voltage generation circuit 112. Olson et al U.S. Pat. No. 5,645,571 further describes and illustrates an AED electrical system like system 100.

Figure 4:
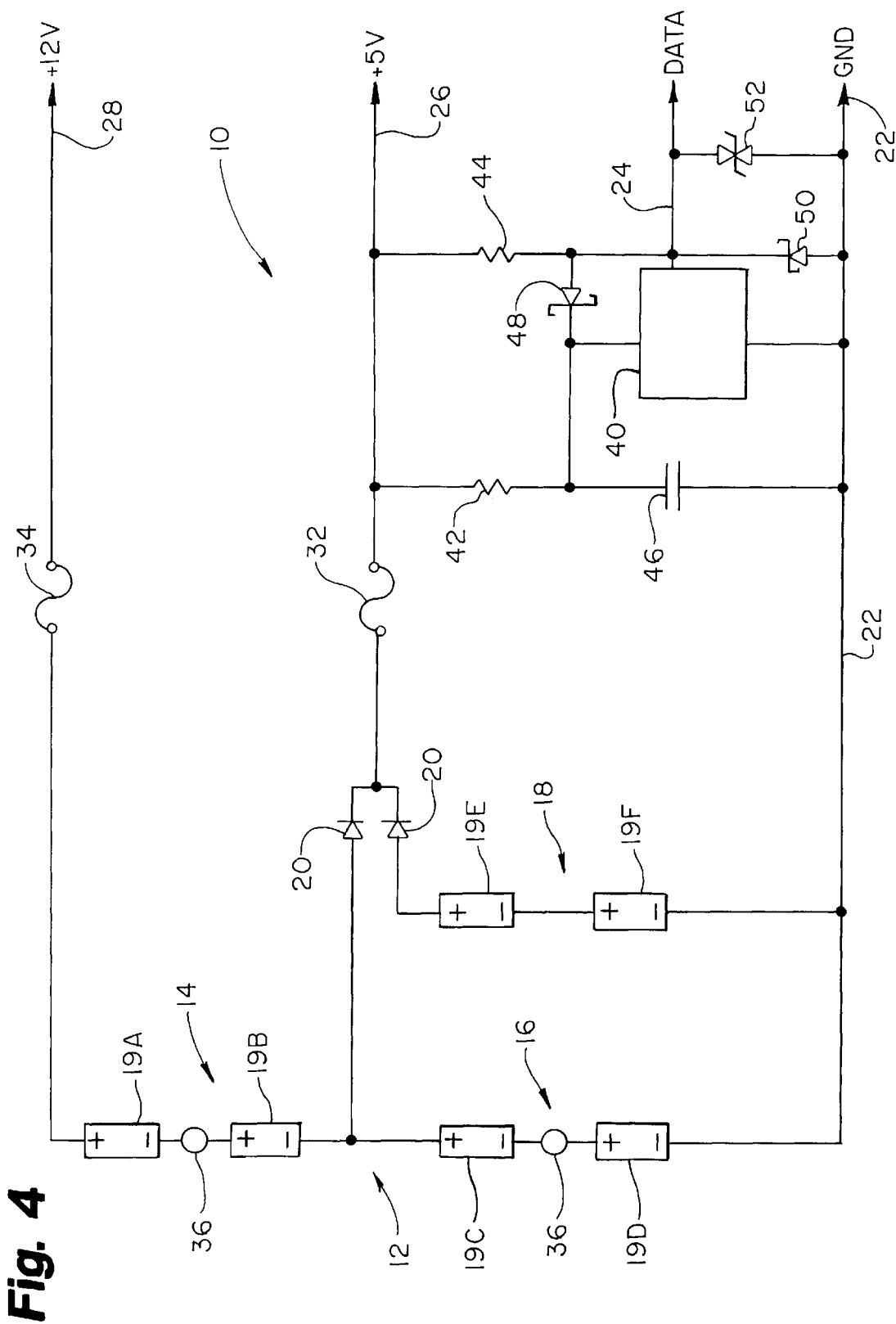
FIG. 4 is a schematic diagram of a preferred embodiment of the dual cell stack battery pack circuit of the present invention.

FIG. 4 is a schematic representation of a dual cell battery circuit 10 of the present invention. Battery pack circuit 10 is housed within battery pack 106 (FIG. 2) for removable insertion and electrical connection within AED case receptacle 108. Battery pack circuit 10 contains first set 12 of battery cells (19A–19D) having upper set 14 of battery cells (19A, 19B) and lower set 16 of battery cells (19C, 19D). Battery pack circuit 10 also contains second set 18 of battery cells (19E, 19F) which are connected in parallel with lower set 16 of cells (19C, 19D). The individual cells (19A–19F) are preferably three volt nominal voltage lithium sulfur dioxide battery cells. However, other types of battery cells could also be used without departing from the spirit or scope of the present invention. Moreover, more or less than six battery cells (19A–19F) can be used to achieve the selected total voltages. With this arrangement, typically 12 V is high current (10A) and 5 V is low current (1A)

In addition, in order to protect lithium cells against reverse biasing in a parallel configuration, battery pack circuit 10 includes a pair of reverse biasing protection diodes 20 connected between second set 18 of cells (19E, 19F) and lower set 16 of cells (19C, 19D). In a preferred embodiment, diodes 20 are IN5819 type diodes known in the art and preferably have a forward voltage drop of about 1 volt. Significantly, diodes 20 are not in the high voltage current path that extends from the top of cell 19A to 12 V output line 28.

As further shown in FIG. 4, battery pack circuit 10 has four electrically conductive leads for connection to an AED including ground or common line 22, serial data line 24, five volt line 26 and 12 volt line 28. Battery pack circuit 10 also includes node 30, one amp fuse 32, seven amp fuse 34, and thermal fuses 36.

Five volt line 26 is connected to the centerpoint of first set 12 of battery cells (19A–19D). In particular, line 26 is connected at the intersection of upper set 14 of cells (19A, 19B), and lower set 16 of cells (19C, 19D) at node 30. One amp fuse 32 is connected between node 30 and the output of line 26 and seven amp fuse 34 is connected between the top of first set 14 of cells (19A) and the output of line 28. This arrangement eliminates the need for a 5 V voltage regulator found in prior art configurations, which managed voltage fluctuations and dips caused by changes in current draw. Larger or smaller fuses may be used for fuses 32 and 34 without departing from the spirit or scope of the present invention. Temperature control fuses 36 are connected between individual cells 19A and 19B of upper cell set 14 and between cells 19C and 19D of lower cell set 16. These temperature fuses prevent the individual cells from overheating.

In the embodiment of FIG. 4, second set 18 of cells (19E, 19F) are used to drive microprocessor 116 and other components of AED 100 while upper set 14 of cells 19A, 19B and either lower set 16 of cells (19C–19D) or second set 18 of cells 19E, 19F are used for charging capacitor bank 114 of AED 100. If needed, lower set 16 of cells (19C, 19D) can be used for operating microprocessor 116 and other components of the AED. Significantly, second set 18 of cells (19E, 19F) cannot be used for charging capacitor bank 114 of AED by virtue of diodes 20. Also, because of the positioning of diodes 20, this battery configuration has the ability to guarantee that one of either lower battery cell set 16 or second battery cell set 18 will fail with the respective other lower set 16 or second set 18 having sufficient power to allow for a controlled shutdown of AED. With this arrangement, AED 100 should never be in the condition where a charge has been delivered from battery pack circuit 10 and the voltage to the processor drops to an unacceptable level causing a malfunctioning processor with a fully charged capacitor bank.

FIG. 4 further includes components for operating battery pack 15 including semiconductor chip 40 connected as known in the art with resistors 42, 44, capacitor 46, diodes 48, 50, and over voltage protection device 52.

Figure 1:
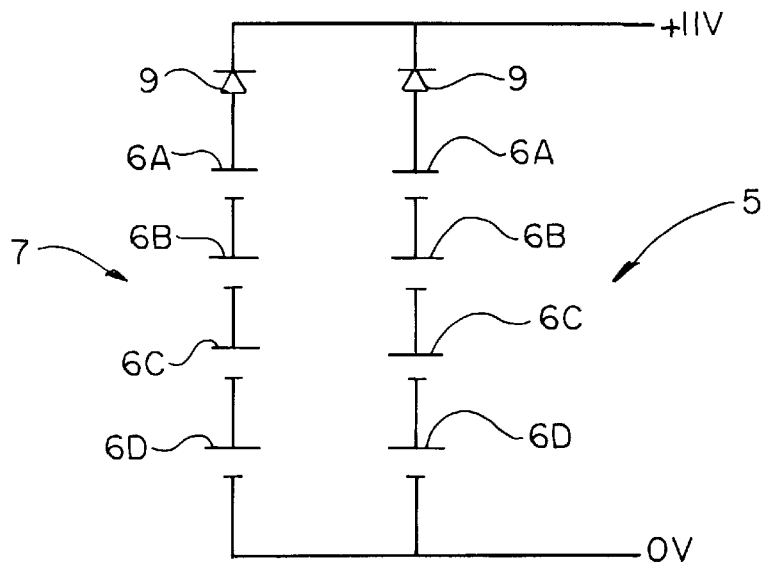
FIG. 1 is a schematic diagram of a typical prior art defibrillator battery pack circuit.

The dual battery stack configuration of battery pack circuit 10 has numerous advantages. First, this arrangement requires only six 3 V cells to provide a 12 V and a 5 V supply whereas the prior art configuration shown in FIG. 1 required eight 3 V cells to provide the same power supply. This reduction in the number of cells results in significant cost savings since each lithium battery cell is expensive, and in space savings since each cell is bulky. Second, by eliminating a reverse bias protecting diode 9 in the 12 V (high voltage) current path (i.e. above cell 19A as shown in FIG. 1), the corresponding voltage drop across the diode (e.g. 0.7 to 1 V) is also eliminated, thereby achieving more power from the expensive lithium batteries. Third, reverse biasing diodes 20 act to limit the power tapped off between the upper and lower set of cells, and the second set of cells, so that a nominal 5 V supply is provided. In a prior art configuration, an extra voltage regulator (in addition to the reverse bias protecting diodes) would be required to provide the 5 V supply. Fourth, lower set 16 of cells and second set 18 of cells provide a redundant or parallel arrangement to insure a reliable 5 V supply. Fifth, the location of the reverse bias diodes 20 insures that the 5 V output will remain constant for microprocessor 116 of AED 100 despite wide variations on the load of the 12 V supply. Sixth, the location of the reverse bias protecting diodes 20, a voltage test for determining the remaining end of life, or battery status of battery pack 10 can be performed without affecting the 5 V power output line. Seventh, the 5 volt output line will always fail last, after a failure of the 12 V line to insure that microprocessor 116 and electrical system 110 retain control of the AED 100 at all times throughout battery life.

Figure 5:
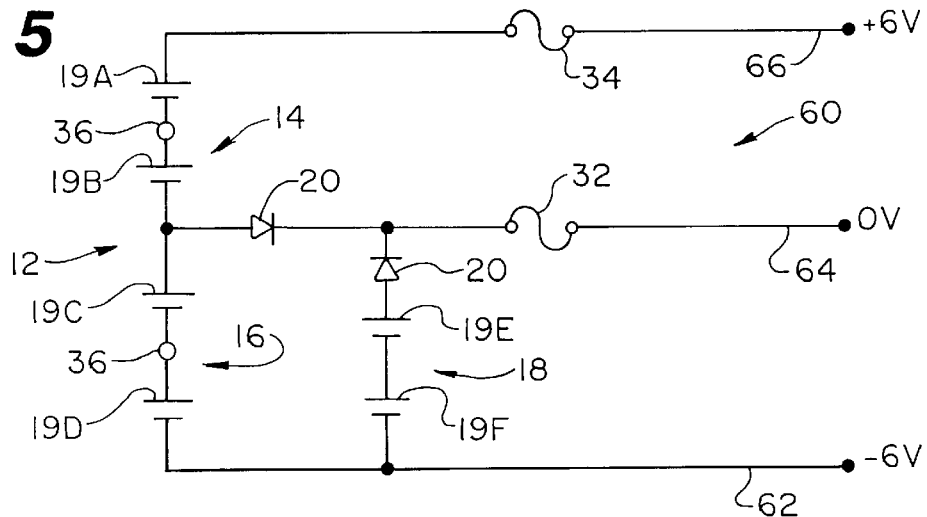
FIG. 5 is a schematic diagram of an alternative embodiment of the dual cell stack battery pack circuit according to the present invention.
Figure 6:
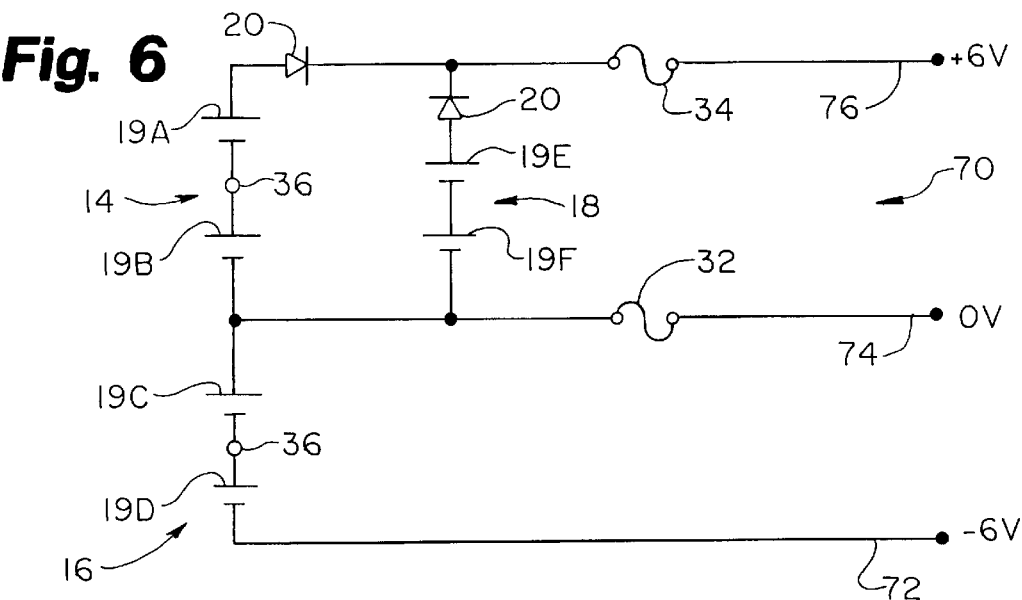
FIG. 6 is a schematic diagram of a further alternative embodiment of the dual cell stack battery pack circuit of the present invention.

FIGS. 5 and 6 illustrate alternative embodiments of battery pack circuit 10 shown in FIG. 4. As can be seen in FIG. 5, alternative battery pack circuit 60 is identical to battery pack circuit 10 except that the output lines are changed from being ground 22, five volt line 26 and 12 volt line 28 to a system having minus six volt line 62, zero volts line 64 and plus six volt line 66 of electrical system of AED 100. As shown in FIG. 6, alternative battery pack circuit 70 is substantially similar to battery circuit 60 except that in battery circuit 70, second set 18 of cells (19E, 19F) is positioned in parallel with upper set 14 of cells (19A, 19B) instead of being in parallel with lower set 16 of cells (19C, 19D). Battery pack circuit 70 includes a system of output lines including a minus 6 V line 72, zero V line 74, and plus 6 V line 76. Diodes 20 are positioned adjacent cells 19A and 19E in a fashion similar to circuit 10.

Battery pack circuit 60 of FIG. 5 and circuit 70 of FIG. 6 are useful when the high voltage supply (12 V total) must be floating relative to the logic circuitry components of AED 100 and for electrical systems otherwise requiring a negative power supply (e.g. −6 V).

Figure 7:
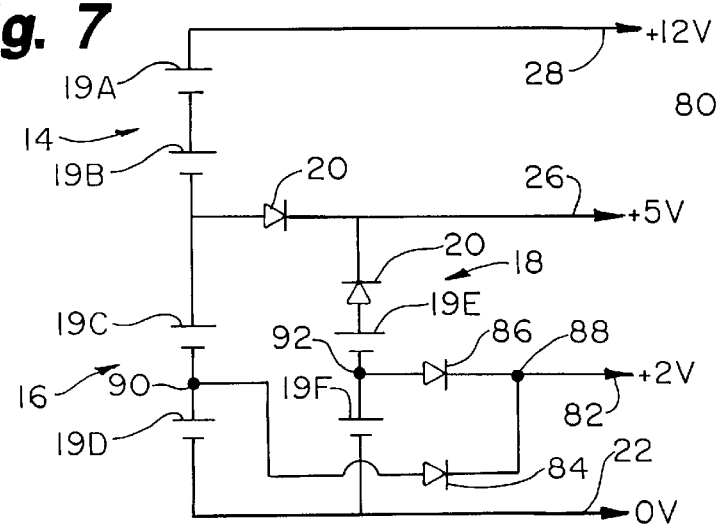
FIG. 7 is a schematic diagram of a further alternative embodiment of the dual cell stack battery pack circuit of the present invention.

FIG. 7 illustrates an alternative battery pack circuit 80 generally similar to battery pack circuit 10 shown in FIG. 4. However, battery pack circuit 80 further incorporates a 2 V output line 82 tapped off battery cell 19D of lower battery cell set 16 and battery cell 19F of second battery cell set 18 and diodes 84 and 86. In this configuration, cell 19D and cell 19F are connected in parallel at node 88 with diode 84 connected between output line node 82 and node 90 (located between lower set 16 cells 19C and 19D) and diode 86 connected between output line node 82 and node 92 (located between second set 18 cells 19E and 19F). As in the prior embodiments, diodes 84 and 86 prevent the reverse biasing of battery cells 19D and 19F when those cells are connected in parallel. The 2 V output line 82 is preferably provided for operating a real time clock, battery backed memory, watch-dog timer, and similar sentinel-type circuit components of an electrical system of AED 100, similar to those components described and illustrated in Olsen et al U.S. Pat. No. 5,645,571, and as shown in FIG. 3. In addition, providing a 2 V output line 82 with diodes 84 and 86 in the parallel battery cell configuration eliminates the need for a voltage regulator in the electrical system that would have been previously necessary to provide a nominal 2 V supply line.

A dual cell stack battery pack of the present invention offers a number of advantages over known battery packs. As stated above, these include, among other things, having the ability to share cells between differing output voltages, guaranteeing a controlled shutdown of the AED, the elimination of a diode from the high voltage current path, the elimination of unnecessary cells and the possibility of expansion to more than two voltages. The elimination of a diode from the high voltage current path is significant due to expensive nature of battery capacity and elimination of the consequential voltage drop that occurs when diode must be implemented in prior art configuration. The battery pack also eliminates need for an external regulator to provide a 5 V supply and the parallel arrangement of lower set and second set of cells establishes greater reliability for 5 V battery. Moreover, the 5 V supply will remain constant even during wide variation on load of 12 V and the first set 12 of cells can be measured under load to predict the end of life of battery without affecting the 5 V rail supply.

In addition, a battery pack of the present invention eliminates two battery cells from prior art battery pack while maintaining same logic battery capacity to support charging and microprocessor. Perhaps most significant, the 5 V battery voltage will always be the last to fail insuring that the microprocessor of AED will safely control the electrical system of AED throughout the battery life of battery pack circuit 10. While the present invention has been described with reference to defibrillators, it may be used with any device requiring batteries.

Although the present invention has been described with reference to preferred embodiments, workers skilled in the art will recognize that changes may be made in form and detail without departing from the spirit or scope of the present invention.

What is claimed is:

1. A battery circuit comprising:
   a first set of battery cells having having a plurality of battery cells coupled in a series arrangement for generating a relatively higher voltage, the first set of battery cells being dividable into a first portion of cells and a second portion of cells, the first and second portions of cells being arranged in series;
   a second set of battery cells arranged in series, the second set of cells connected in parallel with one of the first and second portions of cells for developing a relatively lower voltage, the voltage developed being substantially equal to a voltage developable by the portion of cells being in parallel with the second set of battery cells; and
   a first reverse bias protecting diode operably coupled to the second set of cells and a second reverse biasing protecting diode operably coupled to the portion of cells being in parallel with the second set of battery cells.

2. The battery circuit of claim 1 wherein each battery cell comprises a nominal three volt lithium sulfur dioxide cell.

3. The battery circuit of claim 1 wherein the second reverse bias protecting diode is disposed at the top of the lower set of cells that are connected in parallel to the second set of cells, and the lower set of cells including a pair of cells and the second set of cells including a pair of cells, the battery circuit further comprising:

- a third reverse biasing protecting diode connected between a first node, located between the pair of lower set cells, and a second node defining a 2 V output line of the battery circuit, and
- a fourth reverse biasing protecting diode connected between a third node, located between the pair of second set cells, and the second node.

4. The battery circuit of claim 1 further comprising:
a defibrillator battery pack housing enclosing the battery circuit and being shaped and sized to be removably insertable and electrically connectable to a defibrillator.

5. A battery circuit comprising:
- a first set of battery cells having an upper set of cells arranged in series and a lower set of cells arranged in series;
- a second set of battery cells arranged in series, the second set of cells connected in parallel with at least one cell of the first set of cells, the upper set of cells including two battery cells and the lower set of cells including two battery cells; and
- a first temperature sensing fuse disposed between the two cells of the upper set of cells and a second temperature sensing fuse disposed between the two cells of the lower set of cells.

6. The battery circuit of claim 5 and further comprising a first fuse disposed between the upper set of cells of the first set of battery cells and a 12 V output line of the battery circuit and a second fuse disposed between the lower set of cells of the first set of battery cells and a 5 V output line of the battery circuit.

7. The battery circuit of claim 6 wherein the first fuse is a seven amp fuse and the second fuse is a one amp fuse.

8. A battery circuit comprising:
- a first set of battery cells having an upper set of cells arranged in series and a lower set of cells arranged in series;
- a second set of battery cells arranged in series, the second set of cells connected in parallel with at least one cell of the first set of cells;
- a first reverse bias protecting diode being disposed at the top of the second set of cells and a second reverse biasing protecting diode being disposed at the top of at least one of the upper set of cells and the lower set of cells that are connected in parallel to the second set of cells; and a first output line defined at the top of the upper set of battery cells is a positive six volt supply, a second output line defined at the top of the second set of battery cells is a zero volt ground line, and a third output line defined at the bottom of the lower set of battery cells is a negative six volt supply.

9. An automated external defibrillator battery pack comprising:
- a housing removably mountable to an automated external defibrillator;
- a battery circuit including:
  - a first set of battery cells having an upper set of cells arranged in series and a lower set of cells arranged in series;
  - a second set of battery cells arranged in series, the second set of cells connected in parallel with the lower set of cells;
  - a first reverse bias protecting diode disposed at the top of the second set of cells; and
  - a second reverse biasing diode disposed at the top of the lower set of the first set of cells; and
- a defibrillator battery pack housing enclosing the battery circuit and being shaped and sized to be removably insertable and electrically connectable to a defibrillator.

10. An automated external defibrillator battery pack comprising:
- a housing removably mountable to an automated external defibrillator;
- a battery circuit including:
  - a first set of battery cells having an upper set of cells arranged in series and a lower set of cells arranged in series;
  - a second set of battery cells arranged in series, the second set of cells connected in parallel with the upper set of cells at a first node;
  - a first reverse bias protecting diode disposed between the first node and the top of the second set of cells; and
  - a second reverse biasing diode disposed between the first node and the top of the upper set of the first set of cells,
- wherein the first node defines a positive six volt output line and a second node at the bottom of the lower set of cells defines a negative six volt output line.

* * * * *